(12) United States Patent
Miracle et al.

(10) Patent No.: US 7,425,527 B2
(45) Date of Patent: Sep. 16, 2008

(54) ORGANIC ACTIVATOR

(75) Inventors: Gregory Scot Miracle, Hamilton, OH (US); Robert Richard Dykstra, West Chester, OH (US); George Douglas Hiler, II, Harrison, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 455 days.

(21) Appl. No.: 11/116,775

(22) Filed: Apr. 28, 2005

(65) Prior Publication Data

US 2005/0272631 A1 Dec. 8, 2005

Related U.S. Application Data

(60) Provisional application No. 60/577,277, filed on Jun. 4, 2004.

(51) Int. Cl.
*C11D 7/26* (2006.01)
*C11D 7/32* (2006.01)
*C11D 7/54* (2006.01)

(52) U.S. Cl. ............. 510/313; 252/186.38; 252/186.39; 510/372; 510/376; 510/500; 510/501; 564/152

(58) Field of Classification Search ........................ None
See application file for complete search history.

(56) References Cited

U.S. PATENT DOCUMENTS

| | | | |
|---|---|---|---|
| 2,414,050 A | | 1/1947 | Linch |
| 4,304,833 A | * | 12/1981 | Foley ........................ 430/221 |
| 4,430,243 A | | 2/1984 | Bragg |
| 4,894,358 A | * | 1/1990 | Filosa et al. ................ 503/201 |
| 5,221,603 A | | 6/1993 | Yoneyama et al. |
| 5,360,569 A | | 11/1994 | Madison et al. |
| 5,370,826 A | | 12/1994 | Madison et al. |
| 5,486,303 A | | 1/1996 | Capeci et al. |
| 5,489,392 A | | 2/1996 | Capeci et al. |
| 5,516,448 A | | 5/1996 | Capeci et al. |
| 5,565,422 A | | 10/1996 | Del Greco et al. |
| 5,569,645 A | | 10/1996 | Dinniwell et al. |
| 5,574,005 A | | 11/1996 | Welch et al. |
| 5,576,282 A | | 11/1996 | Miracle et al. |
| 5,595,967 A | | 1/1997 | Miracle et al. |
| 5,597,936 A | | 1/1997 | Perkins et al. |
| 5,691,297 A | | 11/1997 | Nassano et al. |
| 5,718,614 A | | 2/1998 | Armond et al. |
| 5,879,584 A | | 3/1999 | Bianchetti et al. |
| 6,225,464 B1 | | 5/2001 | Hiler, II et al. |
| 6,306,812 B1 | | 10/2001 | Perkins et al. |
| 6,326,348 B1 | | 12/2001 | Vinson et al. |
| 6,417,181 B1 | | 7/2002 | Bender et al. |

FOREIGN PATENT DOCUMENTS

| | | |
|---|---|---|
| EP | 0 032 036 A1 | 7/1981 |
| JP | 04-114147 A | 4/1992 |
| WO | WO91/15474 * | 10/1991 |
| WO | WO 95/07883 A1 | 3/1995 |
| WO | WO98/16608 * | 4/1998 |
| WO | WO 98/16608 A2 | 4/1998 |
| WO | WO 00/32601 A2 | 6/2000 |
| WO | WO 99/37609 A1 | 7/2002 |

OTHER PUBLICATIONS

Runge, Franz et al, The Condensation of Sulfimide Salts with Basic Substituted Alkyl Halides, Chemische Berichte, vol. 86, 1953, pp. 1571-1576.
M. P. Trova et al., Analogues of Platelet Activating Factor. 8. Antagonists of PAF Containing an Aromatic Ring Linked to a Pyridinium Ring, J. Med. Chem vol. 36, No. 5, 1993, pp. 580-590.
Atwell, Graham J. et al., Potential Antitumor Agents. 22. Latentiated Congeners of the 4'-(9-Acridinylamino)methanesulfonanilides Journal of Medicinal Chemistry, vol. 20, No. 4, 1977, pp. 520-526, p. 521, compound 4 in combination with table 1, compounds 14-16, 33-39, 63-66.
Zaoral, M, Amino Acids and Peptides. XXXI. Proucts formed from Tosylglycine under the Conditions of a Mixed Carbonic Anhydride Synthesis Collection of Czechoslovak Chemical Communications, 26, 1961 pp. 2316-2332.
International Search Report (Oct. 2005).

* cited by examiner

*Primary Examiner*—Gregory R Del Cotto
(74) *Attorney, Agent, or Firm*—James F. McBride; Kim William Zerby; Steven W. Miller

(57) ABSTRACT

The present invention relates to organic activators having the following general formula:

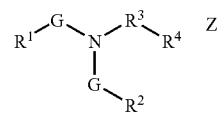

Wherein $R^1$ is a substituted or unsubstituted alkyl or aryl moiety comprising at least five carbons, $R^2$ is a substituted or unsubstituted alkyl moiety comprising less than five carbons, $R^3$ is a suitable bridging moiety, $R^4$ is a charged moiety, N is nitrogen, each G is, independently, an oxygen containing moiety and Z, when present, is a charge balancing counter ion.

The present invention also relates to cleaning compositions comprising said organic activators, and processes for making and using the aforementioned organic activators and cleaning compositions.

34 Claims, No Drawings

ORGANIC ACTIVATOR

CROSS-REFERENCES TO RELATED APPLICATIONS

This application claims priority under 35 U.S.C. § 119(e) to U.S. Provisional Application Ser. No. 60/577,277 filed Jun. 4, 2004.

FIELD OF INVENTION

This invention relates to organic activators and cleaning compositions comprising such activators, and processes for making and using such activators and cleaning products.

BACKGROUND OF THE INVENTION

Oxygen bleaching agents, for example hydrogen peroxide, are typically used to facilitate the removal of stains and soils from clothing and various surfaces. Unfortunately the effectiveness of such agents is extremely temperature rate dependent. As a result, when such agents are employed in colder solutions, the bleaching action of such solutions is markedly decreased.

In an effort to resolve the aforementioned performance problem, the industry developed a class of materials known as "bleach activators". However, such materials suffer side reactions that result in the formation of compounds that are deleterious to certain washing machine components or are essentially insoluble oils that are cost prohibitive to employ in cleaning compositions. Accordingly, there is a need for an improved organic activator.

SUMMARY OF THE INVENTION

The present invention relates to organic activators having the following general formula:

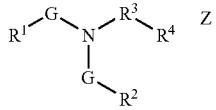

Wherein $R^1$ is a substituted or unsubstituted alkyl or aryl moiety comprising at least five carbons, $R^2$ is a substituted or unsubstituted alkyl moiety comprising less than five carbons, $R^3$ is a suitable bridging moiety, $R^4$ is a charged moiety, N is nitrogen, each G is, independently, an oxygen containing moiety and Z, when present, is a charge balancing counter ion.

The present invention also relates to cleaning compositions comprising said organic activators, and processes for making and using the aforementioned organic activators and cleaning compositions.

DETAILED DESCRIPTION OF THE INVENTION

Definitions

As used herein, the term "cleaning composition" includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, car or carpet shampoos, bathroom cleaners; hair shampoos and hair-rinses; shower gels and foam baths and metal cleaners; as well as cleaning auxiliaries such as bleach additives and "stain-stick" or pre-treat types.

As used herein, the phrase "is independently selected from the group consisting of . . . " means that moieties or elements that are selected from the referenced Markush group can be the same, can be different or any mixture of elements as indicated in the following example:

A molecule having 3 R groups wherein each R group is independently selected from the group consisting of A, B and C. Here the three R groups may be: AAA, BBB, CCC, AAB, AAC, BBA, BBC, CCA, CCB, ABC.

As used herein, "substituted" means that the organic composition or radical to which the term is applied is:

(a) made unsaturated by the elimination of at least one element or radical; or (b) at least one hydrogen in the compound or radical is replaced with a moiety containing one or more (i) carbon, (ii) oxygen, (iii) sulfur, (iv) nitrogen or (v) halogen atoms; or (c) both (a) and (b).

Moieties which may replace hydrogen as described in (b) immediately above, that contain only carbon and hydrogen atoms, are hydrocarbon moieties including, but not limited to, alkyl, alkenyl, alkynyl, alkyldienyl, cycloalkyl, phenyl, alkyl phenyl, naphthyl, anthryl, phenanthryl, fluoryl, steroid groups, and combinations of these groups with each other and with polyvalent hydrocarbon groups such as alkylene, alkylidene and alkylidyne groups. Moieties containing oxygen atoms that may replace hydrogen as described in (b) immediately above include, but are not limited to, hydroxy, acyl or keto, ether, epoxy, carboxy, and ester containing groups. Moieties containing sulfur atoms that may replace hydrogen as described in (b) immediately above include, but are not limited to, the sulfur-containing acids and acid ester groups, thioether groups, mercapto groups and thioketo groups. Moieties containing nitrogen atoms that may replace hydrogen as described in (b) immediately above include, but are not limited to, amino groups, the nitro group, azo groups, ammonium groups, amide groups, azido groups, isocyanate groups, cyano groups and nitrile groups. Moieties containing halogen atoms that may replace hydrogen as described in (b) immediately above include chloro, bromo, fluoro, iodo groups and any of the moieties previously described where a hydrogen or a pendant alkyl group is substituted by a halo group to form a stable substituted moiety.

It is understood that any of the above moieties (b)(i) through (b)(v) can be substituted into each other in either a monovalent substitution or by loss of hydrogen in a polyvalent substitution to form another monovalent moiety that can replace hydrogen in the organic compound or radical.

As used herein, the articles a and an when used in a claim, are understood to mean one or more of what is claimed or described.

Unless otherwise noted, all component or composition levels are in reference to the active level of that component or composition, and are exclusive of impurities, for example, residual solvents or by-products, which may be present in commercially available sources.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All documents cited are, in relevant part, incorporated herein by reference; the citation of any document is not to be construed as an admission that it is prior art with respect to the present invention.

Organic Activator

The present invention relates to organic activators having the general Formula I below:

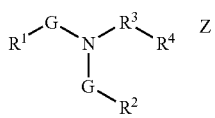

Formula I

Wherein $R^1$ is a substituted or unsubstituted alkyl or aryl moiety comprising at least five carbon atoms, $R^2$ is a substituted or unsubstituted alkyl moiety comprising less than five carbon atoms, $R^3$ is a suitable bridging moiety, $R^4$ is a charged moiety, each G is, independently, an oxygen containing moiety, for example each G can independently be a moiety selected from the group consisting of —C(O)—, —S(O)—, or —S(O)$_2$—, and Z, when present, is a charge balancing counter ion.

While not being bound by theory, it is believed that the combination of the proper selection of the $R^1$ and $R^2$ moieties when coupled with the proper selection of the moieties $R^3$ and $R^4$ results in activators that allow for the formation of hydrophilic and hydrophobic peracids from a single structure, thus providing an improved cleaning profile, while still possessing physical forms, such as solids or pastes, that are amenable for use in cleaning compositions.

In one aspect of Applicants' invention at least one of $R^1$ or $R^2$ is covalently bound directly to at least one of $R^3$ or $R^4$ thus yielding, as a non-limiting example, a structure having Formula II below:

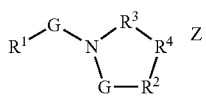

Formula II

In one aspect of Applicants' invention $R^1$ is a substituted or unsubstituted alkyl or aryl moiety comprising from at least 5 to 17 carbon atoms, or alternatively 7 to 13 carbon atoms.

In one aspect of Applicants' invention $R^2$ is a substituted or unsubstituted alkyl moiety comprising from 1 to 2 carbon atoms.

In one aspect of Applicants' invention $R^3$ is selected from a substituted aromatic moiety, unsubstituted aromatic moiety or a moiety having Formula III below:

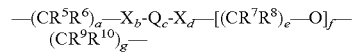

Formula III wherein:
a.) the indices b and c are independently 0 or 1;
b.) the index d is 0 or 1 provided that when c is 0, d is 0;
c.) the indices a and g are independently an integer from 0 to 10;
d.) the index f is an integer from 0 to 20;
e.) the index e is an integer from 1 to 6;
f.) $R^5$, $R^6$, $R^7$, $R^8$, $R^9$ and $R^{10}$ are each independently selected from H, a substituted $C_1$-$C_{20}$ alkyl, an unsubstituted $C_1$-$C_{20}$ alkyl, a substituted $C_4$-$C_{10}$ aryl or heteroaryl, or an unsubstituted $C_4$-$C_{10}$ aryl or heteroaryl;
g.) each X is independently selected from O, S, NR$^{11}$ wherein R$^{11}$ is selected from H, a substituted $C_1$-$C_{20}$ alkyl, an unsubstituted $C_1$-$C_{20}$ alkyl, a substituted $C_4$-$C_{10}$ aryl or heteroaryl, or an unsubstituted $C_4$-$C_{10}$ aryl or heteroaryl; and
h.) Q is CO, SO$_2$, SO, PO or PO$_2$.

In one aspect of Applicants' invention, for Formula III above, the indices c and d may be zero; the indices b, c, d, and f may be zero; or the indices b, c, d, and f may be zero and the indices a and g are each independently an integer from 0 to 3, provided that one of a or g is not 0.

In one aspect of Applicants' invention, for Formula III above, at least one $R^5$, $R^6$, $R^9$ or $R^{10}$ moiety is covalently bound to at least another $R^5$, $R^6$, $R^9$ or $R^{10}$ moiety thus yielding, as a non-limiting example, a structure having Formula IV below:

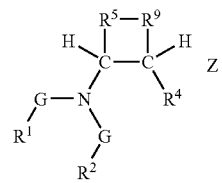

Formula IV

In one aspect of Applicants' invention $R^4$ is an anionic, cationic or zwitterionic moiety comprising less than 20 carbon atoms.

In one aspect of Applicants' invention $R^4$ is:
a.) an anionic moiety selected from the group consisting of carboxylates, carbonates, sulfates, sulfonates, phosphates, or phosphonates;
b.) a cationic moiety selected from the group consisting of ammoniums or pyridiniums; or
c.) a zwitterionic moiety selected from the group consisting of ammonium carboxylates, ammonium sulfates, or ammonium sulfonates.

In one aspect of Applicants' invention Z is:
a.) an anionic moiety selected from the group consisting of halides, preferably chlorides or bromides, carboxylates, carbonates, sulfates, sulfonates, phosphates, or phosphonates; or
b.) a cationic moiety selected from the group consisting of lithium ions, sodium ions, potassium ions, ammonium ions, hydrogen ions, calcium ions or magnesium ions.

In one aspect of Applicants' invention, for Formula I above, a.) $R^1$ is selected from $C_7$ to $C_{11}$ alkyl;
b.) $R^2$ is methyl;
c.) each G is —C(O)—;
d.) $R^4$ is a cationic ammonium having the formula —$N(R^{11})_3$, wherein $R^{11}$ is a $C_1$ to $C_4$ alkyl, or an anionic moiety having the formula —$SO_3$;
e.) Z is a charge balancing counter ion; and
f.) $R^3$ is selected from a substituted aromatic moiety, unsubstituted aromatic moiety or a moiety having Formula III above wherein the indices b, c, d and f are zero, the sum of the indices a and g is an integer from 2 to 6, and each $R^5$, $R^6$, $R^9$ and $R^{10}$ are H.

Processes of Making Organic Activators

The skilled artisan can produce the activators of the present invention by following the teaching contained herein and in the examples. Suitable routes for preparing the organic activators of the present invention include, but are not limited to, contacting a suitable charged amide or sulfamide with one equivalent of a suitable acyl halide or sulfonyl halide to obtain the desired activator. Alternatively, a suitable route for preparing the organic activators of the present invention includes, but is not limited to, contacting a suitable amide or sulfamide comprising a tertiary amine moiety with one equivalent of a suitable acyl halide or sulfonyl halide to form an uncharged activator, followed by contacting such activator with a suitable alkylating agent to obtain the desired charged activator.

Commercial quantities of Applicants' organic activator can be produced using a variety of reaction vessels and processes including batch, semi-batch, and continuous processes. As appreciated by the skilled artisan, reaction conditions vary depending on batch size and vessel type. However, when in possession of the teachings contained herein, such conditions are easily determined.

Cleaning Compositions and Cleaning Composition Additives Comprising Applicants' Organic Activators The cleaning composition of the present invention may be advantageously employed for example, in laundry applications, hard surface cleaning, automatic dishwashing applications, as well as cosmetic applications such as dentures, teeth, hair and skin. Furthermore, the organic activators of the present invention may be employed in both granular and liquid compositions for use in aqueous cleaning applications as well as cleaning compositions that comprise nonaqueous lipophilic solvents such as dry cleaning compositions. A preferred group of nonaqueous lipophilic fluids includes low-volatility nonfluorinated organics, silicones, especially those other than amino functional silicones, and mixtures thereof. Suitable silicones for use as a major component, e.g., more than 50%, of the composition include cyclopentasiloxanes, sometimes termed "D5", and/or linear analogs having approximately similar volatility, optionally complemented by other compatible silicones. Suitable silicones are well known in the literature, see, for example, Kirk Othmer's Encyclopedia of Chemical Technology, and are available from a number of commercial sources, including GE silicone fluids.

The organic activators of the present invention may also be employed in a cleaning additive product. A cleaning additive product including the organic activators of the present invention is ideally suited for inclusion in a wash process when additional bleaching effectiveness is desired. Such instances may include, but are not limited to, low temperature solution cleaning applications. The additive product may be, in its simplest form, Applicants' organic activator. Preferably, the additive could be packaged in dosage form for addition to a cleaning process where a source of peroxygen is employed and increased bleaching effectiveness is desired. Such single dosage form may comprise a pill, tablet, gelcap or other single dosage unit such as pre-measured powders or liquids. A filler or carrier material may be included to increase the volume of such composition. Suitable filler or carrier materials include, but are not limited to, various salts of sulfate, carbonate and silicate as well as talc, clay and the like. Filler or carrier materials for liquid compositions may be water or low molecular weight primary and secondary alcohols including polyols and diols. Examples of such alcohols include, but are not limited to, methanol, ethanol, propanol and isopropanol. Monohydric alcohols may also be employed. The compositions may contain from about 5% to about 90% of such materials. Acidic fillers can be used to reduce pH. Alternatively, the cleaning additive may include an activated peroxygen source defined below and/or the adjunct ingredients as fully defined below.

Applicants, cleaning compositions and cleaning additives require an effective amount of Applicants' organic activator. The required level of such activator may be achieved by the addition of one or more embodiments of Applicants' organic activator. As a practical matter, and not by way of limitation, the compositions and cleaning processes herein can be adjusted to provide on the order of at least 1 ppm of Applicants' organic activator in the washing medium, and will preferably provide from about 1 ppm to about 1500 ppm, more preferably from about 5 ppm to about 1000 ppm, and most preferably from about 10 ppm to about 500 ppm of the organic activator in the wash liquor. In order to obtain such levels of Applicants' organic activator in the wash liquor, typical compositions herein will comprise at least 0.1%, preferably from about 0.5% to about 60%, more preferably from about 0.5% to about 40% by weight of the bleaching composition.

In addition to Applicants' organic activators, certain embodiments of Applicants' cleaning compositions must comprise a material selected from the group consisting of a peroxygen source, hydrogen peroxide and mixtures thereof. Suitable ratios of moles of Applicants' organic activator to moles of peroxygen source include but are not limited to from about 3:1 to about 1:100, from about 1:1 to about 1:50 or alternatively from about 1:2 to about 1:20. Suitable peroxygen sources include, but are not limited to, compounds selected from the group consisting of perborate compounds, percarbonate compounds, perphosphate compounds and mixtures thereof.

When present, hydrogen peroxide sources will typically be at levels of from about 1%, preferably from about 5% to about 30%, preferably to about 20% by weight of the cleaning composition. If present, peracids or additional bleach activators will typically comprise from about 0.1%, preferably from about 0.5% to about 60%, more preferably from about 0.5% to about 40% by weight of the cleaning composition.

In addition to the disclosure above, suitable types and levels of peroxygen and activated peroxygen sources are found in U.S. Pat. Nos. 5,576,282, 6,306,812 B1 and 6,326,348 B1 that are incorporated by reference.

The cleaning compositions herein will typically be formulated such that, during use in aqueous cleaning operations, the wash water will have a pH of between about 6.5 and about 11, or alternatively between about 7.5 and about 10.5. Liquid dishwashing product formulations typically have a pH between about 6.8 and about 9.0. Laundry product formulations typically have a pH of from about 8 to about 11. Techniques for controlling pH at recommended usage levels include the use of buffers, alkalis, acids, etc., and are well known to those skilled in the art.

Adjunct Materials

While not essential for the purposes of the present invention, the non-limiting list of adjuncts illustrated hereinafter are suitable for use in the instant cleaning compositions and may be desirably incorporated in preferred embodiments of the invention, for example to assist or enhance cleaning performance, for treatment of the substrate to be cleaned, or to modify the aesthetics of the cleaning composition as is the case with perfumes, colorants, dyes or the like. The precise nature of these additional components, and levels of incorporation thereof, will depend on the physical form of the composition and the nature of the cleaning operation for which it is to be used. Suitable adjunct materials include, but are not limited to, additional bleach activators, preformed peracids, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, perfumes, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282, 6,306,812 B1 and 6,326,348 B1.

Additional Bleach Activators—Suitable bleach activators that may be used in conjunction with Applicants' organic activator include, but are not limited to, tetraacetyl ethylene diamine (TAED), benzoylcaprolactam (BzCL), 4-nitrobenzoylcaprolactam, 3-chlorobenzoylcaprolactam, benzoyloxybenzenesulphonate (BOBS), nonanoyloxybenzene-sulphonate (NOBS), phenyl benzoate (PhBz), decanoyloxybenzenesulphonate ($C_{10}$-OBS), benzoylvalerolactam (BZVL), octanoyloxybenzenesulphonate ($C_8$-OBS), perhydrolyzable esters, perhydrolyzable carbonates, perhydrolyzable imides and mixtures thereof.

Preformed Peracids—Suitable preformed peracids include, but are not limited to, compounds selected from the group consisting of percarboxylic acids and salts, percarbonic acids and salts, perimidic acids and salts, peroxymonosulfuric acids and salts, and mixtures thereof.

Surfactants—Preferably, the cleaning compositions of the present invention comprise a surfactant or surfactant system wherein the surfactant can be selected from nonionic and/or anionic and/or cationic surfactants and/or ampholytic and/or zwitterionic and/or semi-polar nonionic surfactants.

The surfactant or surfactant system is typically present at a level of from about 0.1%, preferably from about 1%, more preferably from about 5% by weight of the cleaning compositions to about 99.9%, preferably about 80%, more preferably about 35%, most preferably about 30% by weight of the cleaning composition.

Builders—The cleaning compositions of the present invention preferably comprise one or more detergent builders or builder systems. When present, the compositions will typically comprise at least about 1% builder, preferably at least about 5%, more preferably from about 10% to about 80%, preferably to about 50%, more preferably to about 30% by weight of the cleaning composition.

Builders include, but are not limited to, the alkali metal, ammonium and alkanolammonium salts of polyphosphates, alkali metal silicates, alkaline earth and alkali metal carbonates, aluminosilicate builders polycarboxylate compounds, ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Chelating Agents—The cleaning compositions of the present invention may also optionally contain one or more copper, iron and/or manganese chelating agents.

If utilized, chelating agents will generally comprise from about 0.1%, more preferably from about 3.0% to about 15% by weight of the cleaning composition.

Dye Transfer Inhibiting Agents—The cleaning compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof.

When present in the cleaning compositions of the present invention, the dye transfer inhibiting agents are present at levels from about 0.0001%, more preferably from about 0.01%, most preferably from about 0.05% by weight of the cleaning compositions to about 10%, more preferably about 2%, most preferably about 1% by weight of the cleaning composition.

Dispersants—The cleaning compositions of the present invention can also contain dispersants. Suitable water-soluble organic salts are the homo- or co-polymeric acids or their salts, in which the polycarboxylic acid comprises at least two carboxyl radicals separated from each other by not more than two carbon atoms.

Enzymes—The cleaning compositions can comprise one or more enzymes that provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and known amylases, or mixtures thereof. A preferred combination is a cleaning composition having a cocktail of conventional applicable enzymes like protease, lipase, cutinase and/or cellulase in conjunction with the amylase of the present invention.

Enzyme Stabilizers—Enzymes for use in detergents can be stabilized by various techniques including the use of water-soluble sources of calcium and/or magnesium ions in the finished cleaning compositions.

Bleach Boosting Compounds—The cleaning compositions herein may comprise one or more bleach boosting compounds such as a dioxirane, an oxaziridine, or an oxaziridinium or compounds capable of forming such species in situ.

Among suitable bleach boosting compounds for use in accordance with the present invention are cationic imines, zwitterionic imines, anionic imines and/or polyionic imines having a net charge of from about +3 to about −3, and mixtures thereof. These imine bleach boosting compounds of the present invention include those of the general structure:

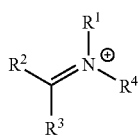

where for Formula V above, $R^1$-$R^4$ may be a hydrogen or an unsubstituted or substituted radical selected from the group consisting of phenyl, aryl, heterocyclic ring, alkyl and cycloalkyl radicals.

Among preferred bleach boosting compounds are zwitterionic bleach boosters, which are described in U.S. Pat. Nos. 5,576,282 and 5,718,614. Other bleach boosting compounds include cationic bleach boosters such as those described in U.S. Pat. Nos. 5,360,569, and 5,370,826.

Catalytic Metal Complexes—Applicants' cleaning compositions may include catalytic metal complexes. One type of metal-containing bleach catalyst is a catalyst system comprising a transition metal cation of defined bleach catalytic activity, such as copper, iron, titanium, cobalt, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methylenephosphonic acid) and water-soluble salts thereof. Such catalysts are disclosed in U.S. Pat. No. 4,430,243.

If desired, the cleaning compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. Nos. 5,597,936, 5,595,967.

Compositions herein may also suitably include a transition metal complex of a macropolycyclic rigid ligand—abbreviated as "MRL". As a practical matter, and not by way of limitation, the compositions and cleaning processes herein can be adjusted to provide on the order of at least one part per hundred million of the active MRL species in the aqueous washing medium, and will preferably provide from about 0.005 ppm to about 25 ppm, more preferably from about 0.05 ppm to about 10 ppm, and most preferably from about 0.1 ppm to about 5 ppm, of the MRL in the wash liquor.

Preferred transition-metals in the instant transition-metal bleach catalyst include nickel, cobalt, manganese, iron and chromium. Preferred MRL's herein are a special type of ultra-rigid ligand that is cross-bridged such as 5,12-diethyl-1,5,8,12-tetraazabicyclo[6.6.2]hexadecane.

Suitable transition metal MRLs are readily prepared by known procedures, such as taught for example in WO 00/332601, and U.S. Pat. No. 6,225,464.

Processes of Making and Using Cleaning Compositions

The cleaning compositions of the present invention can be formulated into any suitable form and prepared by any process chosen by the formulator, non-limiting examples of which are described in U.S. Pat. No. 5,879,584 Bianchetti et al., issued Mar. 9, 1999; U.S. Pat. No. 5,691,297 Nassano et al., issued Nov. 11, 1997; U.S. Pat. No. 5,574,005 Welch et al., issued Nov. 12, 1996; U.S. Pat. No. 5,569,645 Dinniwell et al., issued Oct. 29, 1996; U.S. Pat. No. 5,565,422 Del Greco et al., issued Oct. 15, 1996; U.S. Pat. No. 5,516,448 Capeci et al., issued May 14, 1996; U.S. Pat. No. 5,489,392 Capeci et al., issued Feb. 6, 1996; U.S. Pat. No. 5,486,303 Capeci et al., issued Jan. 23, 1996 all of which are incorporated herein by reference.

Method of Use

The cleaning compositions containing the organic activator disclosed herein can be used to clean a situs inter alia a surface or fabric. Typically at least a portion of the situs is contacted with an embodiment of Applicants' cleaning composition, in neat form or diluted in a wash liquor, and then the situs is optionally washed and/or rinsed. For purposes of the present invention, washing includes but is not limited to, scrubbing, and mechanical agitation. The fabric may comprise most any fabric capable of being laundered in normal consumer use conditions. Such cleaning compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric ratio is typically from about 1:1 to about 30:1.

EXAMPLE I

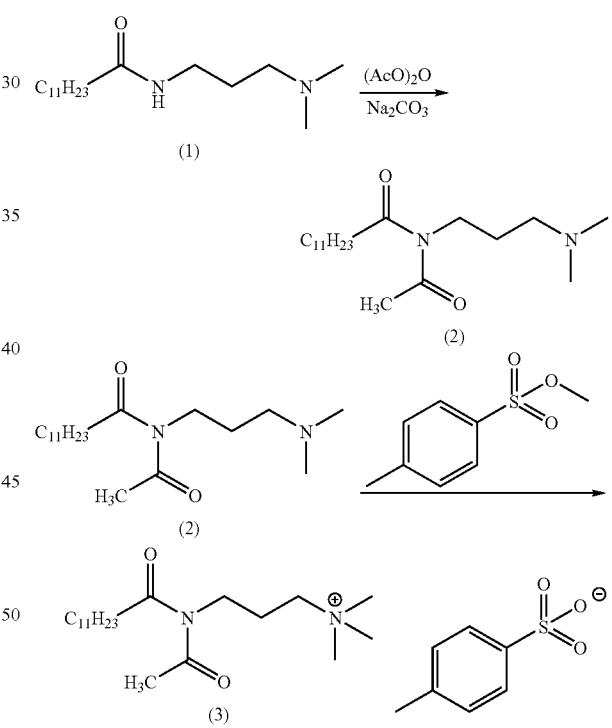

To a flame dried three neck 500 ml round bottomed flask equipped with a condenser, thermometer, heating mantel, magnetic stir bar, magnetic stir plate and dry argon inlet, is added 3-Dodecanamidopropyldimethylamine (1) (Aldrich Chemical Company, Inc., 1001 West Saint Paul Avenue, Milwaukee, Wis., 53233, USA) (10 gm, 35 mmol) and xylenes (Aldrich) (50 ml). To the stirring solution is added 5 equivalents of acetic anhydride (Aldrich) and two equivalents of anhydrous sodium carbonate (Aldrich), and the reaction is warmed to reflux. The reaction is refluxed for 72 hours and allowed to cool to room temperature. The reaction is evaporated to a solid, and the solid is suspended in 200 mL toluene (Aldrich), and washed with three portions (150 ml) of saturated NaHCO₃ (Aldrich). The toluene phase is dried with Na₂SO₄ (Aldrich), filtered and evaporated to an oil. The oil is further purified by high vacuum distillation to yield compound (2). Compound (2) (4.0 gm, 12 mmol) is dissolved in acetonitrile (Aldrich) (50 ml) and the solution is stirred in a 100 ml round bottomed flask equipped with a condenser, argon inlet, magnetic stir bar, and magnetic stir plate, at ambient temperature under a dry argon atmosphere. To the stirring solution is added one equivalent of methyl p-toluenesulfonate (Aldrich) and the reaction is stirred for 24 hours. The solvent is removed under reduced pressure and the resulting solids are dried under vacuum to yield crude compound (3). Compound (3) can be further purified via crystallization.

EXAMPLE II

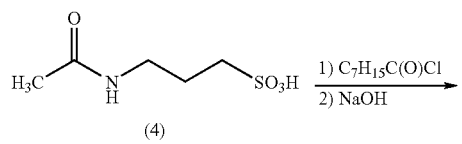

To a flame dried three neck 500 ml round bottomed flask equipped with a condenser, thermometer, heating mantel, magnetic stir bar, magnetic stir plate and dry argon inlet, is added 3-acetylamino-1-propanesulfonic acid (4) (Toronto Research Chemicals Inc., 2 Brisbane Rd. North York, ON, M3J 2J8 Canada) (5 gm, 28 mmol) and xylenes (Aldrich) (50 ml). To the stirring solution is added 1.5 equivalents of octanoyl chloride (Aldrich) and the reaction is warmed to reflux. The reaction is refluxed for 72 hours and allowed to cool to room temperature, after which the solvent is removed under reduced pressure. The resulting solids are dissolved in ethanol and stirred at ambient temperature. To the stirring solution is added 1.1 equivalents of ethanolic sodium hydroxide and the solution is stirred at ambient temperature for 24 hours. The resulting solids are collected by filtration to yield crude compound (5).

EXAMPLE III

To a flame dried three neck 500 ml round bottomed flask equipped with a condenser, thermometer, heating mantel, magnetic stir bar, magnetic stir plate and dry argon inlet, is added 4-Acetamidobenzenesulfonic acid (6) (Aldrich Chemical Company, Inc., 1001 West Saint Paul Avenue, Milwaukee, Wis., 53233, USA) (10 gm, 47 mmol) and anhydrous tetrahydrofuran (Aldrich) (50 ml). To the stirring solution is added 2.1 equivalents of sodium hydride (Aldrich) and the reaction is slowly warmed to reflux and allowed to reflux for 18 hours. After 18 hours the reaction is cooled to ambient temperature. To the reaction vessel is then added 1.1 equivalents of decanoyl chloride and the reaction is again brought to refluxed and refluxed for 72 hours. The reaction is cooled to room temperature and the resulting solids are collected by filtration to yield crude compound (7). Compound (7) can be further purified by re-crystallization from alcohol.

EXAMPLE IV

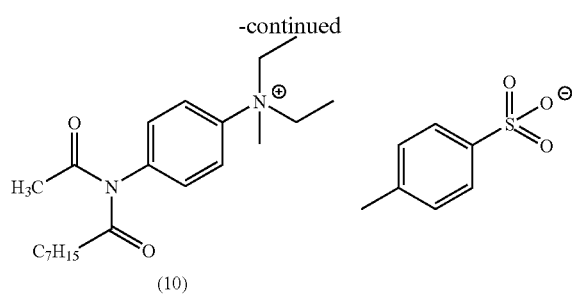

(10)

To a flame dried three neck 500 ml round bottomed flask equipped with a condenser, thermometer, heating mantel, magnetic stir bar, magnetic stir plate and dry argon inlet, is added 4-Diethylaminoacetanilide (8) (ChemBridge Corporation 16981 Via Tazon, Suite G San Diego, Calif., 92127 USA) (2 gm, 10 mmol) and anhydrous tetrahydrofuran (Aldrich) (25 ml). To the stirring solution is added 1.1 equivalents of sodium hydride (Aldrich) and the reaction is slowly warmed to reflux and allowed to reflux for 18 hours. After 18 hours the reaction is cooled to ambient temperature. Once cooled 1.1 equivalents of octanoyl chloride is added to the reaction and the reaction is again brought to reflux, and then refluxed for 72 hours. The reaction is cooled to ambient temperature and the solvent is removed under reduced pressure. The residue is dissolved in toluene (100 ml) and washed with two portions of 0.1N sodium hydroxide (Aldrich), the toluene separated, dried with $Na_2SO_4$, filtered and evaporated to give crude (9). Compound (9) (1.0 gm, 3 mmol) is dissolved in acetonitrile (Aldrich) (10 ml) and the solution stirred in a 50 ml round bottomed flask equipped with a condenser, heating mantel, argon inlet, magnetic stir bar, and magnetic stir plate, at ambient temperature under a dry argon atmosphere. To the stirring solution is added one equivalent of methyl p-toluenesulfonate (Aldrich) and the reaction is warmed to reflux. The solution is refluxed for 24 hours, and allowed to cool to ambient temperature. The solvent is removed under reduced pressure and the resulting solids are dried under vacuum to yield crude compound (10). Compound (10) can be further purified via crystallization from alcohol.

EXAMPLE V

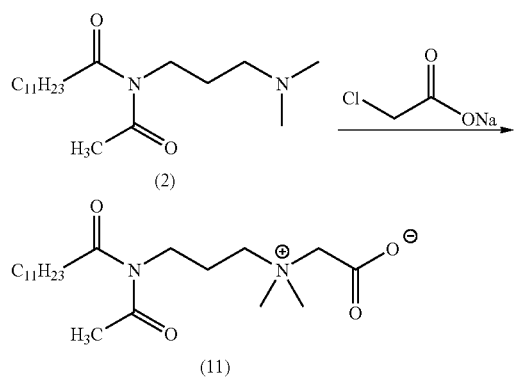

Compound (2) (1.0 gm, 3 mmol), prepared as described in Example I, is dissolved in acetonitrile (Aldrich) (10 ml) and the solution is stirred in a 50 ml round bottomed flask equipped with a condenser, heating mantel, argon inlet, magnetic stir bar, and magnetic stir plate, at ambient temperature under a dry argon atmosphere. To the stirring solution is added one equivalent of chloroacetic acid, sodium slat (Aldrich) and the reaction is warmed to reflux. The solution is refluxed for 24 hours, and allowed to cool to ambient temperature. The solvent is removed under reduced pressure and the resulting solids are dried under vacuum to yield crude compound (11). Compound (11) can be further purified via crystallization.

EXAMPLE VI

Piperazine-2-one is methylated via Eschwiler-Clark reaction. The resulting N-methyl piperazine-2-one is acylated with nonanoyl chloride and the product of the acylation reaction is quaternized via reaction with methyl tosylate to obtain an organic activator according to the present invention, N-nonanoyl-N',N'-dimethylpiperazine-2-one tosylate.

EXAMPLE VII

To a flame dried three neck 500 ml round bottomed flask equipped with a condenser, thermometer, heating mantel, magnetic stir bar, magnetic stir plate and dry argon inlet, is added acetanilide (Aldrich Chemical Company, Inc., 1001 West Saint Paul Avenue, Milwaukee, Wis., 53233, USA) (10 gm, 74 mmol) and anhydrous tetrahydrofuran (Aldrich) (150 ml). To the stirring solution is added 1.1 equivalents of sodium hydride (Aldrich) and the reaction is slowly warmed to reflux and allowed to reflux for 1 hour. After 1 hour the reaction is cooled to ambient temperature. To the reaction vessel is then added 1.1 equivalents of nonanoyl chloride (Aldrich) and the reaction is stirred at 50° C. for 8 hours. The reaction is cooled to room temperature and evaporated to dryness. The resulting solids are suspended in 5% sodium bicarbonate solution (100 ml) and the imide (17) extracted into methylene chloride (150 ml). The organic phase is separated and washed with 2 portions of water (150 ml), the organic phase separated, dried with $Na_2SO_4$ (Aldrich), filtered and evaporated to a semi solid that is crude compound (17). The crude material is added to chlorosulfonic acid (25 ml) and stirred at 60° C. for 2 hours. The reaction is cooled to RT and added drop wise to crushed ice (60 ml). Once addition is complete the resulting solids are collected, washed with water and the solids dissolved in ethanol. To the solution is added 1 equivalent of sodium hydroxide and the resulting solids collected by filtration, washed with ethanol, and dried to afford the desired sodium salt (18).

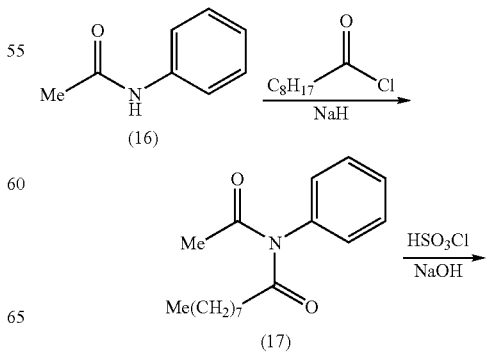

-continued

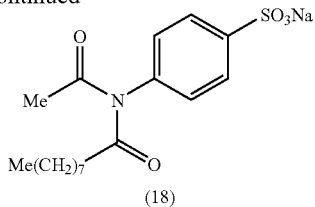

(18)

EXAMPLE VIII

Bleaching compositions having the form of granular laundry detergents are exemplified by the following formulations.

| INGREDIENT | A % | B % | C % | D % | E % |
|---|---|---|---|---|---|
| Bleach Activator[1] | 5 | 3.5 | 1 | 3.5 | 2 |
| Sodium Percarbonate | 0 | 0 | 19 | 21 | 0 |
| Sodium Perborate monohydrate | 21 | 0 | 0 | 0 | 20 |
| Sodium Perborate tetrahydrate | 12 | 21 | 0 | 0 | 0 |
| Tetraacetylethylenediamine | 0 | 0 | 0 | 1 | 0 |
| Nonanoyloxybenzenesulfonate | 0 | 0 | 3 | 0 | 0 |
| Linear alkylbenzenesulfonate | 5.5 | 11 | 19 | 12 | 9.5 |
| Alkyl ethoxylate (C45E7) | 4 | 0 | 3 | 4 | 6 |
| Zeolite A | 20 | 20 | 9.5 | 17 | 21 |
| SKS-6 ® silicate (Hoechst) | 0 | 0 | 11 | 11 | 0 |
| Trisodium citrate | 5 | 5 | 2 | 3 | 3 |
| Acrylic Acid/Maleic Acid copolymer | 4 | 0 | 4 | 5 | 0 |
| Sodium polyacrylate | 0 | 3 | 0 | 0 | 3 |
| Diethylenetriamine penta(methylene phosphonic acid) | 0.4 | 0 | 0.4 | 0 | 0 |
| DTPA | 0 | 0.4 | 0 | 0 | 0.4 |
| EDDS | 0 | 0 | 0 | 0.3 | 0 |
| Carboxymethylcellulose | 0.3 | 0 | 0 | 0.4 | 0 |
| Protease | 1.4 | 0.3 | 1.5 | 2.4 | 0.3 |
| Lipolase | 0.4 | 0 | 0 | 0.2 | 0 |
| Carezyme | 0.1 | 0 | 0 | 0.2 | 0 |
| Anionic soil release polymer | 0.3 | 0 | 0 | 0.4 | 0.5 |
| Dye transfer inhibiting polymer | 0 | 0 | 0.3 | 0.2 | 0 |
| Carbonate | 16 | 14 | 24 | 6 | 23 |
| Silicate | 3.0 | 0.6 | 12.5 | 0 | 0.6 |
| Sulfate, Water, Perfume, Colorants | to 100 | to 100 | to 100 | to 100 | to 100 |

[1]Bleach activator according to any of Examples I-VII

EXAMPLE IX

This Example illustrates bleaching compositions, more particularly, liquid bleach additive compositions in accordance with the invention.

| Ingredients | A wt % | B wt % | C wt % | D wt % |
|---|---|---|---|---|
| NEODOL 91-10[1] | 6 | 11.1 | 7 | 4 |
| NEODOL 45-7[1] | 6 | 3.9 | 5 | 8 |
| NEODOL 23-2[1] | 3 | 0 | 3 | 3 |
| DTPA | .10 | .10 | .10 | .10 |
| Bleach Activator[2] | 3.5 | 3.5 | 2 | 7 |
| Citric Acid | 0.5 | 0.5 | 0.5 | 0.5 |
| NaOH | to pH 4 | to pH 4 | to pH 4 | to pH 4 |
| Hydrogen Peroxide | 6 | 3 | 2 | 7 |
| Water | Balance to 100% | Balance to 100% | Balance to 100% | Balance to 100% |

[1]Alkyl ethoxylate available from The Shell Oil Company.
[2]Bleach Activator according to any of Examples I-VII.

EXAMPLE X

A granular automatic dishwashing detergent composition comprises the following.

| INGREDIENT | A wt % | B wt % | C wt % | D wt % |
|---|---|---|---|---|
| Bleach Activator[1] | 3.5 | 3.5 | 2 | 6.5 |
| Sodium Perborate Monohydrate[2] | 1.5 | 0 | 1.5 | 0 |
| Sodium Percarbonate[2] | 0 | 1.2 | 0 | 1.2 |
| Amylase (TERMAMYL ® from NOVO) | 1.5 | 2 | 2 | 2 |
| Dibenzoyl Peroxide | 0 | 0 | 0.8 | 0 |
| Transition Metal Bleach Catalyst[3] | 0 | 0.1 | 0.1 | 0 |
| Protease (SAVINASE ® 12 T, NOVO, 3.6% active protein) | 2.5 | 2.5 | 2.5 | 2.5 |
| Trisodium Citrate Dihydrate (anhydrous basis) | 7 | 15 | 15 | 15 |
| Citric Acid | 14 | 0 | 0 | 0 |
| Sodium Bicarbonate | 15 | 0 | 0 | 0 |
| Sodium Carbonate, anhydrous | 20 | 20 | 20 | 20 |
| BRITESIL H2O ®, PQ Corp. (as SiO$_2$) | 7 | 8 | 7 | 5 |
| Diethylenetriamine-penta(methylene-phosphonic acid), Na | 0 | 0 | 0 | 0.2 |
| Hydroxyethyldi-phosphonate (HEDP), Sodium Salt | 0 | 0.5 | 0 | 0.5 |
| Ethylenediamindi-succinate, Trisodium Salt | 0.1 | 0.3 | 0 | 0 |
| Dispersant Polymer (Accusol 480N) | 6 | 5 | 8 | 10 |
| Nonionic Surfactant (LF404, BASF) | 2.5 | 1.5 | 1.5 | 1.5 |
| Paraffin (Winog 70 ®) | 1 | 1 | 1 | 0 |
| Benzotriazole | 0.1 | 0.1 | 0.1 | 0 |
| Sodium Sulfate, water, minors balance to: | 100% | 100% | 100% | 100% |

[1]Bleach Activator according to any of Examples I-VII.
[2]These hydrogen peroxide sources are expressed on a weight % available oxygen basis. To convert to a basis of percentage of the total composition, divide by about 0.15.
[3]Transition Metal Bleach Catalyst: Pentaamineacetatocobalt (III) nitrate; may be replaced by MnTACN.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A compound having the formula:

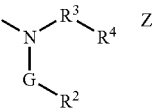

wherein
  a.) $R^1$ is a substituted or unsubstituted alkyl or aryl moiety comprising at least five carbons;

b.) $R^2$ is a substituted or unsubstituted alkyl moiety comprising from one to four carbons;

c.) $R^3$ is a bridging moiety selected from a substituted aromatic moiety, unsubstituted aromatic moiety or a moiety having the formula:

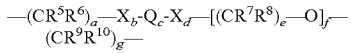

wherein:
 i.) the indices b and c are independently 0 or 1;
 ii.) the index d is 0 or 1 provided that when c is 0, d is 0;
 iii.) the indices a and g are independently an integer from 0 to 10;
 iv.) the index f is an integer from 0 to 20;
 v.) the index e is an integer from 1 to 6;
 vi.) $R^5$, $R^6$, $R^7$, $R^8$, $R^9$ and $R^{10}$ are each independently selected from H, a substituted $C_1$-$C_{20}$ alkyl, an unsubstituted $C_1$-$C_{20}$ alkyl, a substituted $C_4$-$C_{10}$ aryl or heteroaryl. or an unsubstituted $C_4$-$C_{10}$ aryl or heteroaryl;
 vii.) each X is independently selected from O, S, $NR^{11}$ wherein $R^{11}$ is selected from H, a substituted $C_1$-$C_{20}$ alkyl, an unsubstituted $C_1$-$C_{20}$ alkyl, a substituted $C_4$-$C_{10}$ aryl or heteroaryl, or an unsubstituted $C_4$-$C_{10}$ aryl or heteroaryl; and
 viii.) Q is CO, $SO_2$, SO, PO or $PO_2$;

d.) $R^4$ is a charged moiety;

e.) G is —C(O)—, f.) Z, when present, is a charge balancing counter ion; and g.) at least one of $R^1$ or $R^2$ is covalently bound directly to at least one of $R^3$ or $R^4$.

2. A compound according to claim 1 wherein $R^1$ is a substituted or unsubstituted alkyl or aryl moiety comprising from 5 to 17 carbon atoms.

3. A compound according to claim 1 wherein $R^1$ is a substituted or unsubstituted alkyl or aryl moiety comprising from 7 to 13 carbon atoms.

4. A compound according to claim 1 wherein $R^2$ is a substituted or unsubstituted alkyl moiety comprising from 1 to 2 carbon atoms.

5. A compound according to claim 1 wherein for the formula:

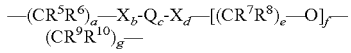

the indices c and d are 0.

6. A compound according to claim 5 wherein for the formula:

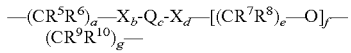

the indices b and f are 0.

7. A compound according to claim 6 wherein for the formula:

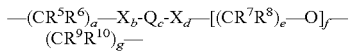

the indices a and g are independently an integer from 0 to 3, provided that one of a or g is not 0.

8. A compound according to claim 1 wherein:
a.) for the formula

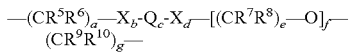

the indices b, c, d and f are zero, the sum of the indices a and g is an integer from 2 to 6, and each $R^5$, $R^6$, $R^9$ and $R^{10}$ are H;

b.) $R^1$ is selected from $C_7$ to $C_{11}$ alkyl;

c.) $R^2$ is methyl;

d.) each G is —C(O)—; and e.) $R^4$ is a cationic ammonium having the formula —$N(R^{11})_3$, wherein $R_{11}$ is a $C_1$ to $C_4$ alkyl, or an anionic moiety having the formula —$SO_3$;

f.) Z is a charge balancing counter ion.

9. A compound according to claim 1 wherein at least one $R^5$, $R^6$, $R^9$ or $R^{10}$ moiety is covalently bound to at least another $R^5$, $R^6$, $R^9$ or $R^{10}$ moiety.

10. A compound according to claim 1 wherein $R^4$ is an anionic, cationic or zwitterionic moiety comprising less than 20 carbon atoms.

11. A compound according to claim 10 wherein $R^4$ is:
a.) an anionic moiety selected from the group consisting of carboxylates, carbonates, sulfates, sulfonates, phosphates, or phosphonates;
b.) a cationic moiety selected from the group consisting of ammoniums or pyridiniums; or
c.) a zwitterionic moiety selected from the group consisting of ammonium carboxylates, ammonium sulfates, or ammonium sulfonates.

12. A compound according to claim 11 wherein $R^4$ is:
a.) an anionic moiety selected from the group consisting of carboxylates, sulfates or sulfonates; or
b.) an ammonium moiety.

13. A compound according to claim 11 wherein $R^3$ is selected from a substituted aromatic moiety, unsubstituted aromatic moiety or a moiety having the formula:

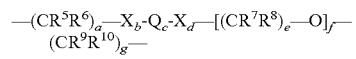

wherein:
a.) the indices b, c, d and f are 0; and
b.) the indices a and g are independently an integer from 0 to 3, provided that one of a or g is not 0.

14. A compound according to claim 1 wherein Z is:
a.) an anionic moiety selected from the group consisting of halides, carboxylates, carbonates, sulfates, sulfonates, phosphates, or phosphonates; or
b.) a cationic moiety selected from the group consisting of lithium ions, sodium ions, potassium ions, ammonium ions, hydrogen ions, calcium ions or magnesium ions.

15. A cleaning composition comprising:
a.) the compound of claim 1;
b.) at least one adjunct ingredient; and
c.) optionally a material selected from the group consisting of a peroxygen source, hydrogen peroxide and mixtures thereof.

16. A cleaning composition comprising:
a.) the compound of claim 8;
b.) at least one adjunct ingredient; and
c.) optionally a material selected from the group consisting of a peroxygen source, hydrogen peroxide and mixtures thereof.

17. The cleaning composition of claim 15, said composition comprising a material selected from the group consisting of a bleach boosting compound, a catalytic metal complex and mixtures thereof.

18. A compound having the formula:

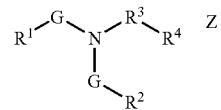

wherein
a.) $R^1$ is a substituted or unsubstituted alkyl or aryl moiety comprising from 5 to 17 carbon atoms;
b.) $R^2$ is a substituted or unsubstituted alkyl moiety comprising from one to four carbons;
c.) $R^3$ is a bridging moiety;
d.) $R^4$ is a charged moiety;
e.) G is —C(O)—
f.) Z, when present, is a charge balancing counter ion.

19. A compound according to claim 18 wherein $R^1$ is a substituted or unsubstituted alkyl or aryl moiety comprising from 7 to 13 carbon atoms.

20. A compound according to claim 18 wherein $R^2$ is a substituted or unsubstituted alkyl moiety comprising from 1 to 2 carbon atoms.

21. A compound according to claim 18 wherein $R^3$ is selected from a substituted aromatic moiety, unsubstituted aromatic moiety or a moiety having the formula:

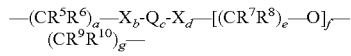

wherein:
a.) the indices b and c are independently 0 or 1;
b.) the index d is 0 or 1 provided that when c is 0, d is 0;
c.) the indices a and g are independently an integer from 0 to 10;
d.) the index f is an integer from 0 to 20;
e.) the index e is an integer from 1 to 6;
f.) $R^5$, $R^6$, $R^7$, $R^8$, $R^9$ and $R^{10}$ are each independently selected from H, a substituted $C_1$-$C_{20}$ alkyl, an unsubstituted $C_1$-$C_{20}$ alkyl, a substituted $C_4$-$C_{10}$ aryl or heteroaryl, or an unsubstituted $C_4$-$C_{10}$ aryl or heteroaryl;
g.) each X is independently selected from O, S, $NR^{11}$ wherein $R^{11}$ is selected from H, a substituted $C_1$-$C_{20}$ alkyl, an unsubstituted $C_1$-$C_{20}$ alkyl, a substituted $C_4$-$C_{10}$ aryl or heteroaryl, or an unsubstituted $C_4$-$C_{10}$ aryl or heteroaryl; and
h.) Q is CO, $SO_2$, SO, PO or $PO_2$.

22. A compound according to claim 21 wherein for the formula:

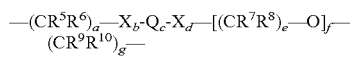

the indices c and d are 0.

23. A compound according to claim 22 wherein for the formula:

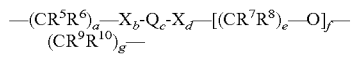

the indices b and f are 0.

24. A compound according to claim 26 wherein for the formula:

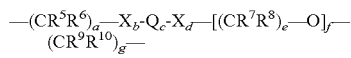

the indices a and g are independently an integer from 0 to 3, provided that one of a or g is not 0.

25. A compound according to claim 21 wherein:
a.) for the formula

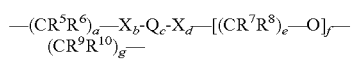

the indices b, c, d and f are zero, the sum of the indices a and g is an integer from 2 to 6, and each $R^5$, $R^6$, $R^9$ and $R^{10}$ are H;
b.) $R^1$ is selected from $C_7$ to $C_{11}$ alkyl;
c.) $R^2$ is methyl;
d.) each G is —C(O)—; and
e.) $R^4$ is a cationic ammonium having the formula —N($R_{11}$)$_3$, wherein $R_{11}$ is a $C_1$ to $C_4$ alkyl, or an anionic moiety having the formula —$SO_3$;
f.) Z is a charge balancing counter ion.

26. A compound according to claim 21 wherein at least one $R^5$, $R^6$, $R^9$ or $R^{10}$ moiety is covalently bound to at least another $R^5$, $R^6$, $R^9$ or $R^{10}$ moiety.

27. A compound according to claim 18 wherein $R^4$ is an anionic, cationic or zwitterionic moiety comprising less than 20 carbon atoms.

28. A compound according to claim 27 wherein $R^4$ is:
a.) an anionic moiety selected from the group consisting of carboxylates, carbonates, sulfates, sulfonates, phosphates, or phosphonates;
b.) a cationic moiety selected from the group consisting of ammoniums or pyridiniums; or
c.) a zwitterionic moiety selected from the group consisting of ammonium carboxylates, ammonium sulfates, or ammonium sulfonates.

29. A compound according to claim 28 wherein $R^4$ is:
a.) an anionic moiety selected from the group consisting of carboxylates, sulfates or sulfonates; or
b.) an ammonium moiety.

30. A compound according to claim 28 wherein $R^3$ is selected from a substituted aromatic moiety, unsubstituted aromatic moiety or a moiety having the formula:

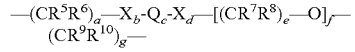

where in
a.) the indices b, c, d and f are 0; and
b.) the indices a and g are independently an integer from 0 to 3, provided that one of a or g is not 0.

31. A compound according to claim 18 wherein Z is:
a.) an anionic moiety selected from the group consisting of halides, carboxylates, carbonates, sulfates, sulfonates, phosphates, or phosphonates; or
b.) a cationic moiety selected from the group consisting of lithium ions, sodium ions, potassium ions, ammonium ions, hydrogen ions, calcium ions or magnesium ions.

32. A cleaning composition comprising:
a.) the compound of claim 18;
b.) at least one adjunct ingredient; and
c.) optionally a material selected from the group consisting of a peroxygen source, hydrogen peroxide and mixtures thereof.

33. A cleaning composition comprising:
a.) the compound of claim 25;
b.) at least one adjunct ingredient; and
c.) optionally a material selected from the group consisting of a peroxygen source, hydrogen peroxide and mixtures thereof.

34. The cleaning composition of claim 32, said composition comprising a material selected from the group consisting of a bleach boosting compound, a catalytic metal complex and mixtures thereof.

* * * * *